United States Patent
Zaken

(10) Patent No.: US 10,849,842 B2
(45) Date of Patent: *Dec. 1, 2020

(54) DISPOSABLE TOOTHBRUSH HAVING TOOTHPASTE COMPOSITION BONDED TO BRISTLES THEREOF

(71) Applicant: Steven Zaken, Brentwood, NY (US)

(72) Inventor: Steven Zaken, Brentwood, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/415,270

(22) Filed: May 17, 2019

(65) Prior Publication Data

US 2019/0269600 A1      Sep. 5, 2019

Related U.S. Application Data

(63) Continuation of application No. 15/333,985, filed on Oct. 25, 2016, now Pat. No. 10,335,360.

(60) Provisional application No. 62/247,489, filed on Oct. 28, 2015.

(51) Int. Cl.

| | | |
|---|---|---|
| *A61K 8/81* | (2006.01) | |
| *A61K 8/73* | (2006.01) | |
| *A46B 9/04* | (2006.01) | |
| *B05D 1/36* | (2006.01) | |
| *B05D 3/00* | (2006.01) | |
| *B05D 3/10* | (2006.01) | |
| *A61Q 11/00* | (2006.01) | |
| *A61K 8/31* | (2006.01) | |
| *A61K 8/33* | (2006.01) | |
| *A61K 8/37* | (2006.01) | |

(52) U.S. Cl.
CPC .............. *A61K 8/8129* (2013.01); *A46B 9/04* (2013.01); *A61K 8/31* (2013.01); *A61K 8/33* (2013.01); *A61K 8/37* (2013.01); *A61K 8/73* (2013.01); *A61K 8/731* (2013.01); *A61Q 11/00* (2013.01); *B05D 1/36* (2013.01); *B05D 3/007* (2013.01); *B05D 3/108* (2013.01); *A46B 2200/1066* (2013.01); *A61K 2800/87* (2013.01); *B05D 2201/02* (2013.01)

(58) Field of Classification Search
CPC .... A46B 2200/1066; A46B 9/04; B05D 1/36; A61Q 11/00
See application file for complete search history.

(56) References Cited

U.S. PATENT DOCUMENTS

| | | | |
|---|---|---|---|
| 4,587,120 A * | 5/1986 | Ozawa | A61K 8/24 424/49 |
| 5,184,719 A | 2/1993 | Gordon | |
| 5,605,756 A | 2/1997 | Sanduja et al. | |
| 5,783,249 A | 7/1998 | Sanduja et al. | |
| 5,888,578 A * | 3/1999 | Sanduja | A46B 11/0003 15/167.1 |
| 6,004,059 A * | 12/1999 | Zaccaria | A46B 11/0003 401/268 |
| 10,335,360 B2 * | 7/2019 | Zaken | A61K 8/731 |
| 2003/0118737 A1 | 6/2003 | Valeri | |

FOREIGN PATENT DOCUMENTS

CN     2404396     11/2000

* cited by examiner

*Primary Examiner* — Robert A Vetere
(74) *Attorney, Agent, or Firm* — Cozen O'Connor

(57) ABSTRACT

A disposable toothbrush having a toothpaste composition distributed over the bristles of the toothbrush without the use of metal graft initiators and catalysts, and in which the toothpaste and the flavoring is maintained for an extended period of time.

20 Claims, No Drawings

DISPOSABLE TOOTHBRUSH HAVING TOOTHPASTE COMPOSITION BONDED TO BRISTLES THEREOF

RELATED APPLICATIONS

This application is a continuation of U.S. patent application Ser. No. 15/333,985 which was filed with the U.S. Patent and Trademark Office on Oct. 25, 2016. This application claims the benefit of U.S. Provisional Application No. 62/247,489, filed Oct. 28, 2015, the entire contents of which is incorporated herein by reference.

BACKGROUND OF THE INVENTION

To accommodate the busy and often harried traveler, disposable toothbrushes have been designed that can be used away from home, for example on a trip, or that can be offered for single use in establishments receiving the public, such as hotels and restaurants. These disposable toothbrushes have eliminated the need for a separate tube of toothpaste by incorporating in or on the brush a sufficient dose of a flavored toothpaste for brushing the teeth, the flavor being added to encourage oral hygiene practices.

Many such prior art disposable toothbrushes are complex and/or expensive, as where a mechanism is included for distributing the toothpaste onto the bristles just prior to use. In other prior art disposable toothbrushes, the toothpaste is preapplied to the bristles, but such toothbrushes have proved unstable, in that the flavoring dissipates after a relatively short period of time, which is impractical as commercial considerations require a reasonable shelf life. As a result, prior art disposable toothbrushes have, for the most part, not proved commercially successful, primarily because no known prior art disposable toothbrush has satisfied the multiple criteria of a preapplied toothpaste thereby eliminating the need for a distribution mechanism, a reasonable shelf life, and a low manufacturing cost.

Other preapplied toothpaste formulations such as those described U.S. Pat. Nos. 5,605,756, 5,783,249, and 5,888,578, all of which are herein incorporated by reference in their entireties, implement a metal ion graft initiator and peroxide catalyst. Generally the amount and types of metal ions and peroxide catalysts used are safe for application in the mouth. However, a formulation omitting these ingredients would be preferable.

SUMMARY OF THE INVENTION

In view of the above, an individually wrapped, inexpensive disposable toothbrush having a toothpaste composition distributed over the bristles of the toothbrush without the use of metal graft initiators and catalysts, and in which the flavoring does not dissipate over a reasonable shelf life is provided.

The compositions and methods described herein generally contemplate bonding toothpaste formulations to bristles of a toothbrush. Some embodiments include a method of bonding a flavored toothpaste composition to a substrate in the absence of a metal graft initiator, peroxide catalyst, or a combination thereof, which include the steps of providing a toothbrush having bristles comprising the substrate, bonding a monomer/prepolymer to the substrate, adding a flavoring to the monomer/prepolymer, adding a physical cross-linking polymer with the bonded monomer/prepolymer, and drying the toothbrush containing the flavored toothpaste composition.

A further embodiment is directed to a method of bonding a flavored toothpaste composition to a substrate, the substrate being the bristles of a toothbrush, which include the steps of applying a prime coat of the toothpaste composition to the bristles of the toothbrush, the prime coat including a monomer/prepolymer, flavoring and other auxiliary excipients; applying a top coat of the toothpaste composition to the prime coat, the top coat comprising a physical cross-linking polymer and other auxiliary excipients; and air drying the toothbrush containing the flavored toothpaste composition.

In some embodiments the substrate includes a functional group selected from the group consisting of amines, amides, imides, alcohols, acids, carbonyls, carboxyls, isocyanates, and combinations thereof.

In some embodiments the substrate includes nylon, polyester, or a combination thereof.

Some embodiments the monomer/prepolymer includes a polyvinyl alcohol, acrylic acid, polyacrylic acid, methacrylic acid, ethyl acrylate, ethyl methacrylate, isobutylmethacrylate, and methyl acrylate.

In some embodiments the physical cross-linking polymer is cellulose gum, carrageenan, or a combination thereof.

In some embodiments the flavoring is menthol, spearmint, or peppermint based.

In some embodiments include the optional step of curing the toothbrush containing the flavored toothpaste composition.

In some embodiments include a step of curing the toothbrush containing the flavored toothpaste composition for about 1 to 5 minutes. In further embodiments the curing is conducted for about one to about two minutes.

Some embodiments adding the flavoring to the polymer chain includes chemical bonding.

In some embodiments adding the flavoring to the polymer chain includes physical bonding.

Some embodiments include growing polymer chains on the substrate.

In another embodiment, a method is disclosed for bonding a flavored toothpaste composition to a substrate in the absence of a metal graft initiator, peroxide catalyst, or a combination thereof, wherein the method involves providing a toothbrush having bristles comprising the substrate, growing polymer chain by chemically bonding a monomer/prepolymer to the substrate, adding a flavoring to the monomer/prepolymer; and adding a physical cross-linking polymer with the bonded monomer/prepolymer, and drying the toothbrush containing the flavored toothpaste composition.

In yet another embodiment, a method is disclosed for bonding a flavored toothpaste composition to a substrate in the absence of a metal graft initiator, peroxide catalyst, or a combination thereof, wherein the method involves providing a toothbrush having bristles comprising the substrate; bonding a monomer/prepolymer to the substrate; adding a flavoring to the monomer/prepolymer; adding a physical cross-linking polymer with the bonded monomer/prepolymer, wherein the physical linking is obtained through, at least partially, intermolecular hydrogen bonding; and drying the toothbrush containing the flavored toothpaste composition

DETAILED DESCRIPTION OF THE EMBODIMENTS

The embodiments of the invention and the various features and advantages thereto are more fully explained with references to the non-limiting embodiments and examples that are described and set forth in the following descriptions of those examples. Descriptions of well-known components and techniques are omitted to avoid obscuring the invention. The examples used herein are intended merely to facilitate an understanding of ways in which the invention may be practiced and to further enable those skilled in the art to practice the invention. Accordingly, the examples and embodiments set forth herein should not be construed as limiting the scope of the invention, which is defined by the claims.

As used herein, terms such as "a," "an," and "the" include singular and plural referents unless the context clearly demands otherwise.

As used herein the term "about" means within 10% of a stated number.

Chemical Grafting

In some of the contemplated embodiments, chemical grafting does not involve a metal graft initiator and/or a catalyst. Instead, carbon-carbon bonds or carbon-nitrogen bonds grow on a substrate via simple reactions, such as condensation reactions, to provide bonding to the substrate without damaging any of the existing positive characteristics of the materials involved. Such polymerizations proceed through step-by-step succession reactions between two functional groups such as amines, amides, imides, alcohols, acids, carbonyls, carboxyls, isocyanates, and other such functional groups. Each of the steps involves the elimination of two reactive sites and results in a new linking unit between a pair of molecules with the elimination of byproducts such as water, alcohol, HCl, or NaCl. For example, in the case of a nylon, crosslinking with a polymer such as polyvinyl alcohol will occur via condensation reactions between the nylon amides and multiple hydroxyl groups comprising the polyvinyl alcohol. Step-growth reactions may also proceed by polyaddition reactions without the elimination of any byproducts such as reactions between diisocyanates with diols.

Further, condensation reactions between two monomers, two oligomers, a monomer and oligomer/macromolecule, or two macromolecules are contemplated within the scope of embodiments. As such, gradual enhancement in the molar mass of the product is inevitable but the reactivity remains equal regardless of molecular weight. The structure of condensation linkages are determined by the functionality of the linking monomers or polymers and the molar ratio of the reactive sites. For example, two bifunctional monomers react to give a linear polymer but when polyfunctional monomers are involved, successively higher conversion leads to branch polymers and the probability of network formation enhances.

One of skill in the art necessarily understands reactions between functional groups that would be suitable for the purposes of crosslinking multiple polymers and/or monomers.

Physical Cross-Linking

Physical cross-linking also affords the advantage of linking polymers with other polymers and/or monomers without the use of metal initiators and catalysts. As such the cross-linking is reversible and provides a relative ease of production when compared to chemical cross-linking and grafting techniques.

In some embodiments, physically cross-linked polymers are formed when cooling hot solutions of carrageenan. The linked network is formed due to helix-formation, association of the helices, and forming junction zones. Carrageenan in hot solution above the melting transition temperature is present as random coil conformation. Without wishing to be bound by theory, when mixed with other polymers, the random carrageenan coils physically intertwine with the other polymers. Then upon cooling the carrageenan transforms to rigid helical rods. In the presence of a salt ($K^+$, $Na^+$, etc.), due to screening the repulsion between sulphonic groups ($SO_3^-$), double helices further aggregate to form a stable matrix. Consequently, the rigid helices provide a physical link with other polymers present when heated. These embodiments are also effective at entrapping other molecules (e.g. flavors).

In some embodiments, the physical cross-linking can be obtained through intermolecular hydrogen bonding. Examples include networks formed by hydrogen-bound cellulose gum (carboxymethylcellulose or CMC). In such systems, the hydrogen bonds between the carboxyl groups induce a decrease in CMC solubility in water and result in the formation of an elastic polymer matrix. A person of skill in the art necessarily understands that similar polymer systems may be formed with functional groups that provide intermolecular hydrogen bonding.

Method of Preparation of the Mint-Flavored Toothpaste Formulation

Some embodiments are directed to a polymeric toothpaste composition that is chemically grafted to the bristles of a toothbrush to form a strong adhesion to the bristles over an extended period of time. As previously stated, chemical grafting does not involve a metal graft initiator and/or a catalyst, and instead, grows carbon-carbon bonds or carbon-nitrogen bonds on a substrate via simple reactions, such as multiple condensation reactions.

The monomers and polymers preferably comprise vinyl alcohol monomers, acrylic, or polyvinyl alcohol polymers, which chemically bond to the bristles. The monomers and prepolymers are preferably acrylic monomers having one or more hydroxyl and carboxyl groups. Some of the monomers and prepolymers of this type are the following: polyvinyl alcohol, acrylic acid, polyacrylic acid, methacrylic acid, ethyl acrylate, ethyl methacrylate, isobutylmethacrylate, and methyl acrylate. Also, mixtures of two or more monomers can be used. Polyvinyl alcohol, acrylic acid and polyacrylic acid are preferred.

The formulation is prepared from a prime coat and a top coat. The prime coat consists basically of the flavoring and the prepolymer and/or monomer, whereas the top coat consists of the polymer providing physical cross-linking properties, pigment and other auxiliary excipients.

The prime coat preferably comprises a polyvinyl alcohol, water, flavor, polysorbate 20, sodium benzoate, potassium sorbate, and methylparaben. The prime coat is applied to the bristles by dipping, then heated at an elevated temperature for 1 to 10 minutes. The amount of prepolymer and/or monomer in the prime coat will normally range from about 0.0001% to about 10.0%, though the preferred concentration ranges from about 3.0% to about 10.0% by weight.

The top coat comprises filler, namely glycerin, hydrated silica, sodium lauryl sulfate, flavor, titanium dioxide, aluminum hydroxide, sodium saccharin, polysorbate 20, trisodium ethylenediaminetetraacetic acid (EDTA), methylparaben, propylparaben, sodium benzoate, and blue 1 (CI 42090), which are combined in a container and mixed until a uniform mix is obtained. The amount of polymer in the top coat will normally range from about 0.0001% to about 10% by weight of the composition, though the preferred concentration ranges from about 0.01% to about 1.0% by weight. A solution of the pigment is prepared, added to the uniform mix, and mixed until a uniform blend is obtained. The desired amounts of the polymers for physical cross-linkage, namely cellulose gum and carrageenan, are then added to the blend and the contents are mixed well. The prepared formulation may then be applied as a top coat over the prime coat by dipping the already flavor-treated toothbrush into the top coat and curing at 300° F. for about 2 minutes.

The amounts of the reactants employed may vary. The total amount of the polymers employed will normally range from about 0.0001% to about 10% by weight of the composition, though the preferred concentration ranges from about 0.1% to about 10% by weight, and a most preferred concentration ranges from about 1.0% to about 7.7% by weight.

Suitable materials for use as flavors are those which allow the user to detect a strong, noticeable flavor while permitting maintenance of an acceptable product appearance. The flavors may be of natural or synthetic origin. Preferably, a menthol based flavor is used. Further suitable flavors include peppermint, spearmint, wintergreen, cinnamon, and the like; fruit flavors such as cherry, strawberry, lime, and the like may also be used. Preferred flavors for use in toothpaste include peppermint, spearmint, and menthol.

Without wishing to be bound by any theory, the flavoring is physically held within a stable polymer matrix provided by a polymer from the top coat such as carrageenan. Further, in the presence of polymers such as cellulose gum, the flavoring is bound through hydrogen bonding. In some embodiments, both carrageenan and cellulose gum are implemented to hold the flavoring within the toothpaste formulation. In some embodiments menthol based flavoring may be chemically bond with the substrate, monomers, and other polymers through condensation reactions as described herein.

Examples of auxiliary excipients utilized in the present invention include fillers, surfactants, buffers and pigments.

In the preferred embodiment of the invention, the bristles of the toothbrush are dipped into a toothpaste that contains monomers, prepolymers, and other excipients of the composition. The coated samples are then air dried at room temperature for approximately 30 to 40 minutes, whereby the hydroxyl and carboxyl groups from the monomers/prepolymers in the toothpaste polymerize to form a strong adhesion to the bristles of the toothbrush.

Certain features and aspects of the present invention are illustrated in the following working examples. The working examples are merely exemplary which are strictly demonstrative and not to be construed as limiting in scope.

Example 1

TABLE 1

| Prime Coat | |
|---|---|
| Ingredient | % Weight |
| Water | 91.15000 |
| Polyvinyl Alcohol | 7.00000 |
| Flavor/Aroma | 1.00000 |
| Polysorbate 20 | 0.10000 |
| Sodium Benzoate | 0.30000 |
| Potassium Sorbate | 0.20000 |
| Limonene | Part of Flavor |
| Methylparaben | 0.25000 |
| Total | 100.00000 |

TABLE 2

| Top Coat | |
|---|---|
| Ingredient | % Weight |
| Water | 40.96727 |
| Glycerin | 35.64000 |
| Hydrated Silica | 16.00000 |
| Sodium Lauryl Sulfate | 2.80000 |
| Flavor/Aroma | 2.00000 |
| Cellulose Gum | 0.40000 |
| Carrageenan | 0.14100 |
| Titanium Dioxide | 0.30000 |
| Aluminum Hydroxide | 0.50000 |
| Sodium Saccharin | 0.50000 |
| Polysorbate 20 | 0.15000 |
| Trisodium EDTA | 0.10000 |
| Methylparaben | 0.25000 |
| Propylparaben | 0.15000 |
| Sodium Benzoate | 0.10000 |
| Cinnamal | Part of Flavor |
| Limonene | Part of Flavor |
| Total | 100.00000 |

What is claimed is:

1. A method of bonding a flavored toothpaste composition to a substrate in the absence of a metal graft initiator, peroxide catalyst, or a combination thereof, comprising the steps of:
   providing a toothbrush having bristles comprising the substrate;
   growing polymer chain by chemically bonding a monomer/prepolymer to the substrate;
   adding a flavoring to the monomer/prepolymer; and
   adding a physical cross-linking polymer with the bonded monomer/prepolymer.

2. The method of claim 1, further comprising drying the toothbrush containing the flavored toothpaste composition.

3. The method of claim 1, wherein the substrate comprises a functional group selected from the group consisting of amines, amides, imides, alcohols, acids, carbonyls, carboxyls, isocyanates, and combinations thereof.

4. The method of claim 1, wherein the substrate comprises nylon, polyester, or a combination thereof.

5. The method of claim 1, wherein the monomer/prepolymer is selected from the group consisting of polyvinyl alcohol, acrylic acid, polyacrylic acid, methacrylic acid, ethyl acrylate, ethyl methacrylate, isobutylmethacrylate, and methyl acrylate.

6. The method of claim 1, wherein the physical cross-linking polymer is cellulose gum, carrageenan, or a combination thereof.

7. The method of claim 1, wherein the flavoring is menthol based.

8. The method of claim 1, wherein the adding a flavoring to the monomer/perpolymer is performed by chemical bonding.

9. The method of claim 1, wherein adding the flavoring to the toothpaste composition comprises physical bonding.

10. The method of claim 1, further comprising the optional step of curing the toothbrush containing the flavored toothpaste composition.

11. A method of bonding a flavored toothpaste composition to a substrate in the absence of a metal graft initiator, peroxide catalyst, or a combination thereof, comprising the steps of:
   providing a toothbrush having bristles comprising the substrate;
   bonding a monomer/prepolymer to the substrate;

adding a flavoring to the monomer/prepolymer;

adding a physical cross-linking polymer with the bonded monomer/prepolymer, wherein the physical linking is obtained through, at least partially, intermolecular hydrogen bonding; and drying the toothbrush containing the flavored toothpaste composition.

12. The method of claim 11, wherein the substrate comprises a functional group selected from the group consisting of amines, amides, imides, alcohols, acids, carbonyls, carboxyls, isocyanates, and combinations thereof.

13. The method of claim 11, wherein the substrate comprises nylon, polyester, or a combination thereof.

14. The method of claim 11, wherein the monomer/prepolymer is selected from the group consisting of polyvinyl alcohol, acrylic acid, polyacrylic acid, methacrylic acid, ethyl acrylate, ethyl methacrylate, isobutylmethacrylate, and methyl acrylate.

15. The method of claim 11, wherein the physical cross-linking polymer is carboxymethylcellulose.

16. The method of claim 11, wherein the flavoring is menthol based.

17. The method of claim 11, wherein adding the flavoring to the toothpaste composition comprises physical bonding.

18. The method of claim 11, further comprising the optional step of curing the toothbrush containing the flavored toothpaste composition.

19. The method of claim 18, further comprising a step of curing the toothbrush containing the flavored toothpaste composition for about 1 to 5 minutes.

20. The method of claim 18, wherein the step of curing is conducted for about one to two minutes.

* * * * *